US009994827B2

(12) United States Patent
Hirao et al.

(10) Patent No.: US 9,994,827 B2
(45) Date of Patent: Jun. 12, 2018

(54) METHOD FOR PRODUCING FRUCTOSYL VALYL HISTIDINE OXIDASE PREPARATION

(71) Applicant: TOYOBO CO., LTD., Osaka-shi, Osaka (JP)

(72) Inventors: Rie Hirao, Tsuruga (JP); Takahide Kishimoto, Tsuruga (JP); Shusaku Yanagidani, Tsuruga (JP)

(73) Assignee: TOYOBO CO., LTD., Osaka (JP)

( * ) Notice: Subject to any disclaimer, the term of this patent is extended or adjusted under 35 U.S.C. 154(b) by 394 days.

(21) Appl. No.: 14/371,288

(22) PCT Filed: Jan. 10, 2013

(86) PCT No.: PCT/JP2013/050259
§ 371 (c)(1),
(2) Date: Jul. 9, 2014

(87) PCT Pub. No.: WO2013/105588
PCT Pub. Date: Jul. 18, 2013

(65) Prior Publication Data
US 2014/0349327 A1 Nov. 27, 2014

(30) Foreign Application Priority Data

Jan. 13, 2012 (JP) ................. 2012-004813
Jan. 13, 2012 (JP) ................. 2012-004814

(51) Int. Cl.
C12N 9/06 (2006.01)
C12Q 1/26 (2006.01)
G01N 33/72 (2006.01)

(52) U.S. Cl.
CPC ......... C12N 9/0032 (2013.01); C12N 9/0022 (2013.01); C12Q 1/26 (2013.01); G01N 33/723 (2013.01)

(58) Field of Classification Search
None
See application file for complete search history.

(56) References Cited

U.S. PATENT DOCUMENTS

| 3,940,480 | A | | 2/1976 | Suenaga et al. | |
|---|---|---|---|---|---|
| 6,033,867 | A | * | 3/2000 | Kato | C12N 9/0022 435/190 |
| 7,485,436 | B2 | * | 2/2009 | Yagi | C09B 67/00 435/25 |
| 8,105,800 | B2 | * | 1/2012 | Kouzuma | C12Q 1/37 435/189 |
| 2003/0157593 | A1 | | 8/2003 | Kurosawa et al. | |
| 2004/0197885 | A1 | | 10/2004 | Ueda et al. | |
| 2011/0195444 | A1 | * | 8/2011 | Hirao | C12N 9/0022 435/25 |
| 2012/0003678 | A1 | | 1/2012 | Aisaka et al. | |

FOREIGN PATENT DOCUMENTS

| JP | S49-006115 A | | 1/1974 |
|---|---|---|---|
| JP | S51-095118 A | | 8/1976 |
| JP | 2005-245315 A | | 9/2005 |
| JP | 2005-261383 A | | 9/2005 |
| JP | 2005245315 A | * | 9/2005 |
| JP | 2006-325547 A | | 12/2006 |
| JP | 4231668 B2 | | 3/2009 |
| JP | 2009-203223 A | | 9/2009 |
| JP | 2010-239969 A | | 10/2010 |
| JP | 4557571 B2 | | 10/2010 |
| JP | 4798600 B2 | | 10/2011 |
| JP | 2011-229526 A | | 11/2011 |
| WO | 2003/004633 A1 | | 1/2003 |
| WO | 2010/041419 A1 | | 4/2010 |
| WO | 2010/041715 A1 | | 4/2010 |
| WO | 2011/126067 A1 | | 10/2011 |

OTHER PUBLICATIONS

JP 2005245315 A English translation of the abstract from JPO.*
Sigma Aldrich Online Catalog (2016).*
Yoshida et al. (1995) Distribution and Properties of Fructosyl Amino Acid Oxidase in Fungi. Applied and Environmental Microbiology 61(12): 4487-4489. Attached with Agenda for Telephone Interview.*
Hirokawa et al. (2003) Biochem Biophys Res Comm 311: 104-111.*
Yoshida et al. (1995) Appl Environ Microbiol 61 (12): 4487-4489.*
Parikh (Apr. 1, 2014) Chemical Engineering. Solids Drying: Basics and Applications.http://www.chemengonline.com/solids-drying-basics-and-applications.*
Ugwu et al. (2004) Pharmaceutical Technology 86-113.*
International Search Report dated Apr. 16, 2013, issued in corresponding application No. PCT/JP2013/050259.
Kim et al., "Motif-Based Search for a Novel Fructosyl Peptide Oxidase From Genome Databases", Biotechnology and Bioengineering, Jun. 15, 2010, pp. 358-366, vol. 106, No. 3.
Notification of Reasons of Refusal dated Nov. 29. 2016, issued in corresponding Japanese Patent Application No. JP2013-002438, with English language translation (15 pages).

* cited by examiner

Primary Examiner — Lisa J Hobbs
(74) Attorney, Agent, or Firm — Westerman, Hattori, Daniels & Adrian, LLP

(57) ABSTRACT

Object
An object of the present invention is to provide a highly stable FVHO preparation and a low-hygroscopicity dried FVHO preparation.
Means for achieving the object
A method for producing a FVHO preparation comprising a step of allowing at least one member selected from phosphoric acid, casein peptone, D-glucosamine hydrochloride, melibiose, sorbose, lactose, fructose, melezitose, glucono-1,5-lactone, and ribitol; and a method for producing a dried FVHO preparation, comprising a step of allowing Bicine to coexist.

3 Claims, No Drawings

METHOD FOR PRODUCING FRUCTOSYL VALYL HISTIDINE OXIDASE PREPARATION

TECHNICAL FIELD

The present invention relates to a method for producing a fructosyl valyl histidine oxidase (hereinafter sometimes referred to as FVHO) preparation, and an FVHO preparation produced by the method. The present invention also relates to a preparation or sensor containing FVHO.

BACKGROUND ART

FVHO acts on fructosyl valyl histidine in the presence of oxygen, and catalyzes a reaction for producing glucosone, valyl histidine, and hydrogen peroxide. Together with protease, FVHO has been conventionally used as a crude enzyme for a hemoglobin A1c measurement reagent, and this enzyme alone has been used for an enzyme sensor. The hemoglobin A1c value in the blood is an indicator of long-term glycemic control. As the source of the FVHO, the genus *Coniochaeta*, genus *Eupenicillium* (Patent Literature 1), genus *Phaeosphaeria* (Patent Literature 2 and Non-patent Literature 1), genus *Emericella* (Patent Literature 3), etc., have been known.

In general, crude enzymes used for reagents or sensors take various preparation forms such as a solution state and a dry state according to the purpose. For example, when used for a hemoglobin A1c measurement reagent, FVHO is often stored in the form present in a solution, and when used for a hemoglobin A1c sensor, FVHO is often stored in the dry state. Further, many of the enzymes used for reagents or sensors are distributed as products in the dry state. (Hereinbelow, preparations in the solution state are sometimes referred to as solution preparations or liquid reagents, and preparations in the dry state are sometimes referred to as dried preparations.)

Products in the dry state (dried preparations) are easy to handle in preservation and transportation because of their lightness and small volume, as well as reduced concern for spoilage by microbial contamination because they are dried. Moreover, products in the dry state can be developed for various applications because the enzyme dissolution concentration can be freely adjusted according to the usage, and the kind of buffer for dissolution can be selected as desired. Further, in general, products in the dry state can stably maintain enzyme activity for a long period of time compared to products in the solution state.

In contrast, preparations in the solution state (solution preparations) do not need to be dissolved at the time of use; therefore, operation is simple, which advantageously reduces the probability of contamination and mistaking one solution for another.

For liquid reagents, even when the stability is poor, correct results can be obtained as long as calibration is performed in each measurement using a reference material; however, since calibration is not performed in sensors, further improvement in storage stability is required.

In any form of use, addition of a stabilizing agent to protect an enzyme protein and prevent modified deactivation is essential. A stabilizing agent to be added to an enzyme product requires not only the ability during formation into products to prevent modified deactivation of an enzyme protein due to drying but also the ability to prevent activity loss during storage or distribution process.

To produce a dried preparation, various means can be used to make an enzyme in the dry state. Examples include a method in which an object enzyme is precipitated from a solution containing an enzyme protein using an organic solvent such as acetone and alcohol, thus collecting the object enzyme to form a dry powder; a spray-dry method in which a solution containing an enzyme is nebulized, followed by drying with hot air; and a freeze-drying method in which a solution containing an enzyme is frozen, followed by drying under reduced pressure.

When an enzyme is dried, problems such as activity loss due to protein modification and generation of turbidity matter during redissolution may occur. In many such cases, a stabilizing agent to protect an enzyme protein and prevent modified deactivation is added.

A known method for stabilizing a freeze-dried preparation of an enzyme having FVHO activity is the technique of allowing ethylenediaminetetraacetic acid and sodium glutamate, or calcium chloride and trehalose to coexist with the enzyme to freeze-dry the enzyme (refer to Patent Literature 4).

A known method for stabilizing an FVHO solution preparation is the technique of adding ethylenediaminetetraacetic acid and allowing at least one member selected from the group consisting of ammonium sulfate, xylitol, and glycine to coexist with FVHO to freeze-dry the FVHO (refer to Patent Literature 5).

CITATION LITERATURE

Patent Literature

PTL 1: JP4231668B
PTL 2: WO2010/041419
PTL 3: WO2010/041715
PTL 4: JP4557571B
PTL 5: JP4798600B

Non-Patent Literature

NPL 1: Biotechnology and Bioengineering, Vol. 106, 358-366 (201)

SUMMARY OF INVENTION

Technical Problem

An object of the present invention is to provide a highly stable FVHO preparation. Further, in view of application to a sensor, etc., for the purpose of providing a method for using FVHO in a more preferable manner in the dry state, the present inventors newly examined the compositions added to the dried FVHO preparations used in the prior art.

The hygroscopicity of additives worsens sensor performance. Specifically, amino acids such as sodium glutamate have hygroscopicity presumably because they have hydrophilic groups such as amino groups and carboxyl groups, and the hydrophilic groups adsorb water. Regarding salts, calcium chloride and like salts are known to have deliquescency.

For example, in a sensor in which an enzyme preparation is mounted in the freeze-dry state on the surface of the sensor, and a very small amount of a liquid sample and the enzyme preparation are mixed and dissolved during measurement to start a reaction, when an enzyme-containing dried preparation absorbs moisture, the retained moisture dilutes the enzyme concentration during measurement or makes the preparation a clay-like or syrup-like form, preventing rapid dissolution, thus sometimes leading to a shortage of a reagent component in the early stage of the reaction. In the latest sensors, the amount of an enzyme to be used may be kept to the minimum for reducing costs, in which case, a slight shortage of a reagent component results in variations in enzyme reaction speed, which may reduce measurement accuracy.

The inventors newly found the above problem relating to the hygroscopicity of a dried FVHO preparation, which had not been mentioned previously. Additionally, a method for improving the hygroscopicity of a dried FVHO preparation was not previously known.

The present invention was made in view of the above problem. Accordingly, an object of the present invention is to provide a low-hygroscopicity dried FVHO preparation.

Solution to Problem

As a result of extensive research, the inventors found that the problems can be solved by the means shown below, and attained the present invention. Specifically, the present invention includes the following structures.

Item 1. A method for producing a dried FVHO preparation, comprising a step of allowing Bicine to coexist.

Item 2. The method for producing a dried FVHO preparation according to Item 1, comprising a step of allowing melibiose to coexist.

Item 3. A method for producing an FVHO preparation comprising a step of allowing at least one member selected from (A) below to coexist:

(A): phosphoric acid, casein peptone, D-glucosamine hydrochloride, melibiose, sorbose, lactose, fructose, melezitose, glucono-1,5-lactone, and ribitol.

Item 4. A dried FVHO preparation comprising Bicine.

Item 5. The dried FVHO preparation according to Item 3, comprising melibiose.

Item 6. An FVHO preparation comprising at least one member selected from (A) below to coexist:

(A): phosphoric acid, casein peptone, D-glucosamine hydrochloride, melibiose, sorbose, lactose, fructose, melezitose, glucono-1,5-lactone, and ribitol.

Item 7. A hemoglobin A1c measurement reagent comprising a dried FVHO preparation according to any one of Items 4 to 6.

Item 8. A hemoglobin A1c sensor comprising a dried FVHO preparation according to any one of Items 4 to 6.

Item 9. A method for measuring hemoglobin A1c using the hemoglobin A1c measurement reagent or the hemoglobin A1c sensor according to Item 7 or 8.

Advantageous Effects of Invention

The present invention can ensure the stability of an FVHO preparation, thus preventing enzyme deactivation even after long-term storage.

Moreover, the present invention can reduce the hygroscopicity of a dried FVHO preparation.

DESCRIPTION OF EMBODIMENTS

The present invention is described below in detail. FVHO used in the present invention is an oxidase that acts on fructosyl peptide in the presence of oxygen to produce valyl histidine, glucosone, and hydrogen peroxide. Any oxidase can be included as long as it is an enzyme that has the above effect. The FVHO used in the present invention may be of any origin, and may be recombinantly produced.

In the present invention, the FVHO preparation indicates a preparation containing the FVHO mentioned above. Typical examples include dried preparations and solution preparations (liquid reagents).

In the present invention, the dried FVHO preparation indicates a preparation obtained through a step of drying a composition containing the above FVHO using a drying means that a person skilled in the art would generally use, such as freeze-drying or air-drying. The drying means is not particularly limited, and examples include a method in which an object enzyme is precipitated from a solution containing an enzyme protein by an organic solvent such as acetone and alcohol, thus collecting the object enzyme to form a dry powder; a spray-dry method in which a solution containing an enzyme is nebulized, followed by drying with hot air; and a freeze-drying method in which a solution containing an enzyme is frozen, followed by drying under reduced pressure.

Freeze-drying is preferable to prevent enzyme deactivation to the extent possible. Air-drying is also preferable because enzyme deactivation can be prevented by suitably controlling the drying temperature and time.

Embodiment 1

The method for producing an FVHO preparation of the present invention includes a step of allowing at least one reagent selected from (A) shown below to coexist in the production of the FVHO preparation:

(A) phosphoric acid, casein peptone, D-glucosamine hydrochloride, melibiose, sorbose, lactose, fructose, melezitose, glucono-1,5-lactone, and ribitol.

Various commercially available reagents can be used as (A).

The purpose of adding at least one reagent listed in (A) above is to improve the stability of the FVHO preparation; thereofore, the addition amount can be suitably determined as long as the purpose is attained. Accordingly, the concentration of the reagent listed in (A) above is not particularly limited; however, in a dried preparation, the lower limit of the FVHO and the reagent listed in (A) above is preferably in a weight ratio of 2:1, and more preferably 1:1. From the viewpoint of the risk of introducing impurities, the upper limit of the FVHO and (A) is preferably in a weight ratio of 1:2. In a solution preparation, from the viewpoint of the risk of introducing impurities, the upper limit is preferably 200 mM or less, more preferably 100 mM or less, even more preferably 50 mM or less, even more preferably 30 mM or less, and even more preferably less than 20 mM. From the viewpoint of stability improvement, the lower limit is preferably 1 mM or more, and more preferably 5 mM or more.

When the preparation is a solution preparation, the amount of the reagent listed in (A) above in the preparation can be presumed with high accuracy without any treatment. When the preparation is a dried preparation, the amount of the reagent listed in (A) above in the preparation can be presumed with high accuracy by subjecting a solution obtained by dissolving the preparation in a suitable amount of a solution such as water to an analysis such as chromatography, e.g., HPLC, and titration using perchloric acid, a chelating reagent, etc.

In addition to the above components, the FVHO preparation of the present invention may include, as necessary, an optional component, and the composition of the preparation is not particularly limited.

As a buffer, the composition is not particularly limited; however, a buffer having buffering ability in a range of pH 4 to 9 is preferable. Examples of the buffer include buffering agents such as boric acid, tris chloride, and potassium phosphate; and good buffering agents such as ACES, BES, Bicine, Bis-Tris, CHES, EPPS, HEPES, HEPPSO, MES, MOPS, MOPSO, PIPES, POPSO, TAPS, TAPSO, TES, and Tricine. Other examples include buffering agents based on dicarboxylic acids such as phthalic acid, maleic acid, or glutaric acid. These may be used singly, or two or more of them may be used. Further, these may be used in a combination with at least one compound other than the above.

The buffer may include, as necessary, a chelating agent such as EDTA and/or a surfactant. The addition concentration of the chelating agent and/or the surfactant is not particularly limited as long as buffering ability is exhibited; however, the upper limit is preferably 100 mM or less, more preferably 50 mM or less, and the lower limit is preferably 5 mM or more. The amount of the buffering agent in a dry powder or a freeze-dried product is not particularly limited, and it is preferably 0.1% (weight ratio) or more, and more preferably in a range of 0.1 to 80% (weight ratio). For these agents, various commercially available reagents can be used.

To produce a dried preparation, the concentration of an enzyme liquid to be subjected to a drying step is adjusted so that the protein concentration is preferably 5 g/L or more, more preferably 10 g/L or more, and even more preferably 20 g/L or more. When the enzyme to be subjected to the drying step is too dilute, the collection rate in the drying step is reduced in many cases, which often makes the form of the resulting dry product difficult to handle. In contrast, when the enzyme concentration is too high, drying may take time.

Another embodiment of the present invention is a hemoglobin A1c measurement reagent containing the FVHO preparation, or a hemoglobin A1c sensor containing the preparation. Still another embodiment of the present invention is a method for measuring hemoglobin A1c using the hemoglobin A1c measurement reagent or the hemoglobin A1c sensor. These can be produced by incorporating the FVHO preparation prepared by the above method in the reagent or sensor according to any of various known methods. Using such a reagent or sensor, hemoglobin A1c can be measured according to a known method.

Stability improvement mentioned in the present invention indicates that the residual rate (%) of FVHO retained after storage at 37° C. for one week is increased or at least maintained compared to the case where no stabilizing agent is added.

Specifically, stability improvement was determined as follows.

In the activity measurement method disclosed in the method for measuring FVHO enzyme activity described later, the (a) FVHO oxidase activity value per weight of a dry product obtained after drying and the (b) FVHO oxidase activity value per weight of a dry product obtained after storage at a certain temperature for a certain period were measured, and the relative value ((b)/(a)×100) wherein the value (a) was assumed to be 100 was obtained. The relative value obtained was considered to be a residual rate. In comparing a case where the compound was added to a case where it was not added, the stability was considered to be improved when the residual rate was increased by the addition of the compound.

Embodiment 2

The method for producing a dried FVHO preparation of the present invention includes a step of allowing Bicine to coexist in the production of a dried FVHO preparation. Bicine is one of the good buffering agents and is a typical buffering agent widely used in the field of biochemistry. Commercially available products of Bicine can be easily obtained.

The purpose of adding Bicine is to suppress the hygroscopicity of the dried FVHO preparation; therefore, the addition amount can be suitably determined as long as the purpose is attained. Accordingly, the concentration of the Bicine is not particularly limited; however, the lower limit of the FVHO and Bicine is preferably in a weight ratio of 2:1, and more preferably 1:1. From the viewpoint of the risk of introducing impurities, the upper limit of the FVHO and Bicine is preferably in a weight ratio of 1:2.

The amount of the Bicine in the dried preparation can be presumed with high accuracy by dissolving the preparation in a suitable amount of a solution such as water, followed by perchloric acid titration, titration using a chelating effect of Bicine, or the like.

The method for producing a dried FVHO preparation of the present invention may further include a step of allowing another material to coexist for the purpose of stabilizing the FVHO preparation. The materials are not particularly limited, and examples include casein peptone, D-glucosamine hydrochloride, melibiose, sorbose, lactose, fructose, melezitose, glucono 1,5-lactone, ribitol, etc. Of these, melibiose, D-glucosamine hydrochloride, and sorbose are preferable, and melibiose is more preferable. Various commercially available reagents can be used as the materials.

The addition amount of each of these compounds can be suitably determined as long as the stabilizing purpose can be attained. Accordingly, the concentration of each compound allowed to coexist is not particularly limited; however, the lower limit of the FVHO and the compound is preferably in a weight ratio of 2:1. From the viewpoint of the risk of introducing impurities, the upper limit of the FVHO and the compound is preferably in a weight ratio of 4:3.

In the method for producing a dried FVHO preparation of the present invention, a dried preparation having both good hygroscopicity and good stability can be obtained by adding Bicine and melibiose.

The concentration of the Bicine is preferably such that the weight ratio of FVHO:Bicine is 2:1 to 1:2, and the concentration of melibiose is such that the weight ratio of FVHO:melibiose is 2:1 to 4:3. The concentration of Bicine is more preferably such that the weight ratio of FVHO:Bicine is 1:1 to 1:2, and the concentration of melibiose is more preferably such that the weight ratio of FVHO:melibiose is 2:1 to 4:3.

The amount of the compound in the dried preparation can be presumed with high accuracy by dissolving the preparation in a suitable amount of a solution such as water, and using HPLC or other like means.

In addition to the above components, the dried FVHO preparation of the present invention may include, as necessary, an optional component, and the composition of the preparation is not particularly limited.

As a buffer, the buffering ability of Bicine mentioned above can be used, but a buffer having buffering ability in the range of pH 4 to 9 can be suitably added. Examples of the buffer include buffering agents such as boric acid, tris chloride, and potassium phosphate; and good buffering agents such as ACES, BES, Bis-Tris, CHES, EPPS, HEPES, HEPPSO, MES, MOPS, MOPSO, PIPES, POPSO, TAPS, TAPSO, TES, and Tricine. Other examples include buffering agents based on dicarboxylic acids such as phthalic acid, maleic acid, or glutaric acid. These may be used singly, or two or more of them may be used. Further, these may be used in a combination with at least one compound other than the above.

The buffer may include, as necessary, a chelating agent such as EDTA and/or a surfactant. The addition concentration of the chelating agent and/or the surfactant is not particularly limited as long as buffering ability is exhibited; however, the upper limit is preferably 100 mM or less, more preferably 50 mM or less, and the lower limit is preferably 5 mM or more. The amount of the buffering agent in a dry powder or a freeze-dried product is not particularly limited; however, it is preferably used in an amount of 0.1% (weight ratio) or more, and more preferably in a range of 0.1 to 80% (weight ratio). Various commercially available reagents can be used as the chelating agent and the surfactant.

The concentration of an enzyme liquid to be subjected to a drying step is adjusted so that the protein concentration is preferably 5 g/L or more, more preferably 10 g/L or more, and even more preferably 20 g/L or more. When the enzyme to be subjected to the drying step is too dilute, the collection rate is reduced in the drying step in many cases, which often makes the form of the resulting dry product difficult to handle. In contrast, when the enzyme concentration is too high, drying sometimes takes time.

Another embodiment of the present invention is a dried FVHO preparation containing Bicine. The dried preparation can be produced by using any one of the methods described above, and can be formed into a dry powder or freeze-dried preparation.

In another embodiment of the present invention, the dried preparation may further include another component in addition to FVHO to form a hemoglobin A1c measurement reagent, or a hemoglobin A1c sensor including the dried preparation.

Still another embodiment of the present invention is a method for measuring hemoglobin A1c using the hemoglobin A1c measurement reagent or hemoglobin A1c sensor.

According to the present invention, the hygroscopicity of the dried FVHO preparation can be reduced. Low hygroscopicity mentioned in the present invention indicates the state where the powder does not become a clay-like form and does not adsorb to a spatula, etc., when the freeze-dried FVHO preparation is stored at a humidity of 70% and 25° C. for 7 hours, and then the powder is mixed with the spatula.

EXAMPLES

The present invention is explained below with reference to the Examples; however, the present invention is not limited thereto. Table 1 shows the composition of an activity measurement reagent used in the Examples. The reagents used in the Examples were purchased from Nacalai Tesque Inc., unless otherwise specified.

TABLE 1

| Activity measurement reagent | |
|---|---|
| Peroxidase from Horseradish | 5000 U/L |
| F-VH | 2 mM |
| 4-Aminoantipyrine | 0.01% (W/V) |
| Phenol | 0.02% (W/V) |
| MES pH 6.5 | 50 mM |

FVHO Activity Measurement Conditions in Examples

Measurement Principle

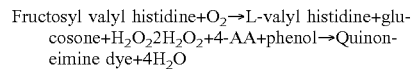

Fructosyl valyl histidine+$O_2$→L-valyl histidine+glucosone+$H_2O_2$ $2H_2O_2$+4-AA+phenol→Quinoneimine dye+$4H_2O$ Two molecules of hydrogen peroxide ($H_2O_2$) formed by the FVHO-catalyzed reaction, 4-amino antipyrin (4-AA), and phenol underwent oxidative condensation by a reaction catalyzed by the peroxidase present in the solution, thereby forming a quinoneimine dye. The presence of this dye was determined by spectrophotometry at 500 nm.

Definition of Unit

One unit is defined as the enzyme amount of FVHO that forms one micromole of $H_2O_2$ per minute under the following conditions.

Method

Preparation of Reagents

A. 0.5% (w/v) 4-AA solution
B. 1.5% (w/v) phenol solution
C. 500 U/mL peroxidase (produced by Toyobo Co., Ltd.; product code: PEO-301) solution
D. 50 mM MES buffer (pH of 6.5)
E. 1.0 mg/mL fructosyl valyl histidine aqueous solution (prepared at the time of use)
F. Enzyme dilution solution: 50 mM potassium phosphate buffer containing 0.1% Triton X-100 (pH of 6.5)
G. Powder solution: 50 mM potassium phosphate buffer (pH of 6.5)

Procedure

1. The following reaction mixture was prepared in a light shielding bottle and stored on ice (prepared at the time of use).

0.4 mL 1.5% phenol solution (A)
0.6 mL 0.5% 4-AA solution (B)
0.3 mL 500 U/mL peroxidase solution (C)
3.7 mL 50 mM MES buffer (pH of 6.5) (D)

The reaction mixture (2.5 ml) and (E) (0.5 mL) were placed in a test tube, followed by preliminary heating at 37° C. for about 5 minutes.

The enzyme solution (0.1 mL) was added thereto and gently mixed.

While keeping the mixture at 37° C., an increase in absorbance for water at 500 nm was recorded for 2.5 minutes, and AOD per minute from 1 minute to 2.5 minutes was calculated (AOD test).

At the same time, the same method except for adding the enzyme dilution solution (F) in place of the enzyme solution was repeated to measure a blank (ΔOD blank).

The enzyme powder was dissolved in the ice-cooled powder solution (G) just before the assay, and diluted with the enzyme dilution solution (F) to 0.5 to 0.1 U/mL.

Calculation

The activity is calculated using the following formulae:

$$U/mL = \{\Delta OD/\min(\Delta OD\text{test} - \Delta OD\text{blank}) \times Vt \times df\} / (13.3 \times \frac{1}{2} \times 1.0 \times Vs)$$

$$U/mg = (U/mL) \times 1/C$$

Vt: Total volume (3.1 mL)
Vs: Sample volume (0.1 mL)
13.3: mmol molecular absorbance coefficient (cm²/μmol) of quinoneimine dye under the above measurement conditions.
½Factor based on the fact that one mole of $H_2O_2$ generated by the enzyme reaction produces half a mole of quinoneimine dye.
1.0: Light path length (cm)
df: Dilution factor
C: Enzyme concentration during dissolution (c mg/mL)

Example 1: Examination of Additives (1)

Preparation of Dried Preparation

First, solutions based on a phosphate buffer (50 mM, pH of 6.5), each containing FVHO and a different additive were prepared.

As the FVHO, product FPO-301, produced by Toyobo Co., Ltd., was used, which was prepared so that A280 (absorbance at 280 nm) equaled 40.

The concentration of each additive was calculated based on the enzyme concentration (A280=1 was determined to be 1 mg/mL. Each additive was added in a concentration (weight ratio) of 50% of the enzyme concentration. Specifically, each additive was added at a final concentration of 20 mg/ml because A280 equaled 40 in the enzyme concentration. (In this case, the enzyme and the additive in the dried preparation were in a weight ratio of 2:1.) After the addition of the FVHO and each additive, filtration (pore size: 0.2 μm) was performed. The resultant was dispensed into a vial in an amount of exactly 2 mL. A control containing no additive was also prepared. Each resultant was vacuum-freeze-dried (FDR) to completely evaporate moisture, and then pulverized to a powder using a spatula.

Hygroscopic Test

Subsequently, about 10 mg of the powder was accurately measured and placed in a spitz tube stored at a humidity of 70%, 25° C., for 7 hours, and then mixed with a spatula. The powder was evaluated according to the following criteria.
++ The powder had the same form as that before moisture absorption.
+ The power was not the same as that before adsorption, but did not become a clay-like form and not adsorb to the spatula.
− The powder became a clay-like form or adsorbed to the spatula.

Stability Test

About 10 mg of a powder was accurately measured in a spitz tube. (1) The FVHO activity was measured immediately (the activity value obtained here is referred to as (a)), and (2) measured after storage for one week at 37° C. (the activity value obtained here is referred to as (b)). The activity per weight of powder was calculated. Regarding the residual activity ratio, the relative value ((b)/(a)×100) wherein the measurement value (a) was assumed to be 100% was calculated. This relative value is considered to be the residual ratio.

Table 2 shows the results. Regarding stability, the residual activity ratio increased when casein peptone, D-glucosamine hydrochloride, melibiose, sorbose, lactose, fructose, melezitose, glucono 1,5-lactone, ribitol, or sorbose was added compared to when nothing was added. Of these, melibiose showed the highest residual activity ratio. In contrast, in the results of the hygroscopic test, form deterioration was observed in most of the cases that included an additive.

TABLE 2

| Additive composition | Residual activity ratio (%) | Form after moisture absorption |
|---|---|---|
| No additive | 62.9 | ++ |
| Casein peptone | 78.1 | + |
| L-ornithine hydrochloride | 84.2 | + |
| Glycylglycine | 88.1 | + |
| Lactose | 92.8 | − |
| Fructose | 95.5 | − |
| Melezitose | 96.0 | − |
| Glucono-1,5-lactone | 97.6 | − |
| Ribitol | 100.2 | − |
| Sorbose | 100.9 | − |
| D-glucosamine hydrochloride | 102.7 | + |
| Melibiose | 103.8 | − |

Example 2: Examination of Buffers

Change in the composition of the buffer was examined. The composition and the method were according to Example 1, and buffers having a concentration of 50 mM and a pH of 6.5 were used. Consequently, when buffers other than the phosphoric acid were used, the stability was reduced compared to when the phosphate buffer was used (Table 3). This surprisingly indicates that phosphoric acid had a stabilizing effect.

TABLE 3

| Buffer composition | Residual activity ratio (%) |
|---|---|
| Phosphoric acid | 62.9 |
| MES | 53.3 |
| Bis-Tris | 40.5 |
| Bicine | 55.2 |
| Maleic acid | 45.7 |
| Phthalic acid | 43.1 |
| Citric acid | 33.4 |

Example 3: Examination of Phosphoric Acid Concentration Generating Turbidity Matter during Mixing with Blood Sample The phosphate buffer whose stabilizing effect was proved in Example 2 has a wide buffering area and is easily available at low cost; however, coexistence of phosphoric acid and calcium is generally known to form calcium phosphate, thus generating turbidity. Since blood contains calcium, when a powder contains phosphoric acid, turbidity is generated, which may prevent the correct measurement of absorbance. The mixing concentration of the phosphate buffer and calcium was therefore examined to see whether turbidity matter would be generated.

The composition and method were according to Example 1. The maximum concentration of calcium in the blood was 10 mg/dL, and the turbidity was measured by mixing the calcium and a solution containing a different concentration of a phosphate buffer. Specifically, (1) 20 mg/dL calcium chloride aqueous solutions and (2) solutions each containing a 60, 50, 40, 30, 20, or 10 mM potassium phosphate aqueous solution wherein the pH was 6.5 were prepared. Subsequently, (1) and (2) were each mixed at a ratio of 1:1 to measure turbidity (OD 660 nm).

Consequently, the turbidity was below the detection limit when the final phosphoric acid concentration was less than 20 mM (Table 4). Thus, there is no problem if phosphoric acid is added in a manner such that the final phosphate buffer concentration is less than 20 mM when the powder is dissolved. In the case where an FVHO-containing hemoglobin A1c measurement liquid reagent is practically applied to a widely used automatic analyzer, since the sample is diluted to about ten times to tens of times, there is no problem if the upper limit of the addition amount of phosphoric acid is about 200 mM, preferably 100 mM, and more preferably about 50 mM. Specifically, it was found that by using phosphoric acid, which is not generally preferable for a liquid reagent, the FVHO solution preparation of the present invention surprisingly causes no problem of generation of turbidity, but, rather, improves stability.

Note that since a sensor directly detects a current value, generation of some turbidity is allowable.

TABLE 4

| Final phosphate buffer concentration (mM) | OD 660 (Abs) |
|---|---|
| 30 | 0.14 |
| 25 | 0.14 |
| 20 | 0.11 |
| 15 | N.D. |
| 10 | N.D. |
| 5 | N.D. |
| 0 | N.D. |

Example 4: Confirmation of Effect of Stabilizing Agent Using Buffers Other than Phosphate Buffer Subsequently, each of the stabilizing agents shown in Table 2 was examined as to whether it exhibited an effect only when allowed to coexist with a phosphate buffer, or regardless of the composition of a buffer. The method was according to Example 2. The buffers used were Bicine, which showed the highest residual activity ratio, and citrate, which showed the lowest residual activity ratio in Example 2.

Consequently, even when buffers other than the phosphate buffer were used, each of the additives shown in Example 2 similarly exhibited a stability improvement effect (Table 5).

TABLE 5

| Buffer composition | Additive composition | Residual activity ratio (%) |
|---|---|---|
| Bicine | No additive | 55.2 |
| | Casein peptone | 68.5 |
| | L-ornithine hydrochloride | 73.9 |
| | Glycylglycine | 77.3 |
| | Lactose | 81.4 |
| | Fructose | 83.8 |

TABLE 5-continued

| Buffer composition | Additive composition | Residual activity ratio (%) |
|---|---|---|
| | Melezitose | 84.3 |
| | Glucono-1,5-lactone | 85.6 |
| | Ribitol | 87.9 |
| | Sorbose | 88.5 |
| | D-glucosamine hydrochloride | 90.1 |
| | Melibiose | 97.8 |
| Citric acid | No additive | 33.4 |
| | Casein peptone | 41.5 |
| | L-ornithine hydrochloride | 44.7 |
| | Glycylglycine | 46.8 |
| | Lactose | 52.1 |
| | Fructose | 50.7 |
| | Melezitose | 51.0 |
| | Glucono-1,5-lactone | 51.8 |
| | Ribitol | 53.2 |
| | Sorbose | 53.6 |
| | D-glucosamine hydrochloride | 54.5 |
| | Melibiose | 70.3 |

Example 5: Examination of Additives (2)

Subsequently, to improve the form after moisture absorption obtained when melibiose, which showed the highest residual activity ratio in Example 2, was allowed to coexist, additives to be mixed with the melibiose were examined.

The dried preparation was produced in the same manner as in Example 1. In the production of a solution containing FVHO and an additive, product FPO-301, produced by Toyobo Co., Ltd., was used as the FVHO, which was prepared so that A280 (absorbance at 280 nm) equaled 40. Melibiose was added at two different levels, i.e., in a concentration (weight ratio) of 50% (final concentration: 20 mg/mL) or 25% (final concentration: 10 mg/mL) of the enzyme concentration. (In this case, the weight ratios of the enzyme and this additive in the dried preparation were respectively 2:1 and 4:1.) The concentration of the other additive was 50% of the enzyme concentration (final concentration: 20 mg/mL). (In this case, the weight ratio of the enzyme and the other additive in the dried preparation was 2:1.) After the addition, powderization was performed according to the same procedure as in Example 1.

Table 6 shows the results. Hygroscopicity was improved when the melibiose concentration was reduced, and any member selected from the group consisting of L-ornithine hydrochloride, Bicine, glycylglycine, casein peptone, and poly vinyl pyrrolidone 25 was added. In particular, the hygroscopicity was good when the Bicine was added. In contrast, stability was reduced when the melibiose concentration was reduced.

TABLE 6

| Melibiose concentration (enzyme:melibiose weight ratio) | Additive composition | Form after moisture absorption | Residual activity ratio (%) |
|---|---|---|---|
| 4:1 | No additive | − | 55.4 |
| 4:1 | Bicine | ++ | 47.7 |
| 4:1 | Glycylglycine | + | 62.1 |
| 4:1 | Casein peptone | + | 90.5 |
| 4:1 | Polyvinylpyrrolidone 25 | + | 51.8 |
| 2:1 | No additive | − | 103.8 |

TABLE 6-continued

| Melibiose concentration (enzyme:melibiose weight ratio) | Additive composition | Form after moisture absorption | Residual activity ratio (%) |
|---|---|---|---|
| 2:1 | Bicine | − | — |
| 2:1 | Glycylglycine | − | — |
| 2:1 | Casein peptone | − | — |
| 2:1 | Polyvinylpyrrolidone 25 | − | — |

Example 6: Optimization of Melibiose and Bicine Concentrations

Subsequently, the melibiose concentration and the Bicine concentration were optimized.

The dried preparation was produced in the same manner as in Example 1. In the production of a solution containing FVHO and an additive, product FPO-301 produced by Toyobo Co., Ltd. was used as the FVHO, which was prepared so that A280 (absorbency at 280 nm) equaled 40. Melibiose was added at three different levels, i.e., in a concentration (weight ratio) of 75% (final concentration: 30 mg/mL), 50% (final concentration: 20 mg/mL), or 25% (final concentration 10 mg/mL) of the enzyme concentration. (In this case, the weight ratios of the enzyme and this additive in the dried preparation were respectively 4:3, 4:2 (2:1), and 4:1.) Bicine was also added at three different levels, i.e., in a concentration (weight ratio) of 200% (final concentration: 80 mg/mL), 100% (final concentration: 40 mg/mL), or 50% (final concentration 20 mg/mL) of the enzyme concentration. (In this case, the weight ratios of the enzyme and this additive in the dried preparation were respectively 1:2, 1:1, and 2:1.) After the addition, powderization was performed according to the same procedure as in Example 1.

Table 7 shows the results. It was found that when the melibiose concentration and the Bicine concentration were both increased, the hygroscopicity was improved while ensuring stability.

Regarding the addition amount of Bicine, it was confirmed that the hygroscopicity was improved when the FVHO and Bicine were added in a weight ratio ranging from 2:1 to 1:2, preferably 1:1 to 1:2.

In these circumstances, when the FVHO and melibiose were added in a weight ratio ranging from 2:1 to 4:3, it was confirmed that good stability was ensured.

TABLE 7

| Melibiose concentration (enzyme:melibiose weight ratio) | Bicine concentration (enzyme:Bicine weight ratio) | Form after moisture absorption | Residual activity ratio (%) |
|---|---|---|---|
| 4:1 | 0 | − | 55.4 |
| 4:1 | 2:1 | ++ | 47.7 |
| 4:1 | 1:1 | ++ | 48.9 |
| 4:1 | 1:2 | ++ | 49.5 |
| 4:2 (2:1) | 0 | − | 103.8 |
| 4:2 (2:1) | 2:1 | + | 88.5 |
| 4:2 (2:1) | 1:1 | ++ | 86.4 |
| 4:2 (2:1) | 1:2 | ++ | 87.1 |
| 4:3 | 0 | − | 100.3 |
| 4:3 | 2:1 | + | 91.8 |
| 4:3 | 1:1 | ++ | 92.3 |
| 4:3 | 1:2 | ++ | 95.1 |

INDUSTRIAL APPLICABILITY

According to the present invention, the stability of the FVHO preparation can be improved, and the hygroscopicity of the freeze-dried FVHO preparation can be reduced, thereby improving stability. These preparations can be used for stabilizing enzyme sensors based on the principles of electrochemistry. Accordingly, the present invention can contribute to the further diffusion of clinical examination based on preventive medicine.

The invention claimed is:

1. A method for producing a dried fructosyl valyl histidine oxidase preparation, comprising:
    mixing Bicine and melibiose with fructosyl valyl histidine oxidase liquid to obtain a mixture, and
    drying the mixture,
    wherein a ratio of fructosyl valyl histidine oxidase to the melibiose in the fructosyl valyl histidine oxidase liquid is 2:1 to 4:3, and
    wherein a ratio of fructosyl valyl histidine oxidase to the Bicine in the fructosyl valyl histidine oxidase liquid is 2:1 to 1:2.

2. The method according to claim 1, further comprising mixing at least one additive selected from the group consisting of casein peptone, D-glucosamine hydrochloride, sorbose, lactose, fructose, melezitose, glucono 1,5-lactone, ribitol, L-ornithine hydrochloride, and glycylglycine with the fructosyl valyl histidine oxidase liquid, prior to drying the mixture.

3. The method according to claim 2,
    wherein only one additive selected from the group consisting of casein peptone, D-glucosamine hydrochloride, sorbose, lactose, fructose, melezitose, glucono 1,5-lactone, ribitol, L-ornithine hydrochloride, and glycylglycine is mixed with the fructosyl valyl histidine oxidase liquid, prior to drying the mixture, and
    wherein the amount of the additive is at least half of the amount of fructosyl valyl histidine oxidase in the fructosyl valyl histidine oxidase liquid, by weight.

* * * * *